(12) United States Patent
Boschetti et al.

(10) Patent No.: US 7,530,539 B2
(45) Date of Patent: May 12, 2009

(54) POLE TOP SUPPORT FOR AERIAL ELECTRIC POWER LINES

(75) Inventors: Mario Boschetti, Donnas (IT); Claudio Boschetti, Donnas (IT)

(73) Assignee: Conveytech S.r.l., Turin (IT)

( * ) Notice: Subject to any disclaimer, the term of this patent is extended or adjusted under 35 U.S.C. 154(b) by 866 days.

(21) Appl. No.: 10/362,721

(22) PCT Filed: Aug. 27, 2001

(86) PCT No.: PCT/IB01/01546

§ 371 (c)(1),
(2), (4) Date: May 23, 2003

(87) PCT Pub. No.: WO02/19493

PCT Pub. Date: Mar. 7, 2002

(65) Prior Publication Data

US 2004/0113026 A1 Jun. 17, 2004

(30) Foreign Application Priority Data

Aug. 28, 2000 (IT) ............................ TO2000A0822

(51) Int. Cl.
*A47G 29/00* (2006.01)
(52) U.S. Cl. .................. 248/219.2; 248/218.4; 52/76.2; 174/148

(58) Field of Classification Search ................. 248/499, 248/65, 218.4, 219.2, 904, 219.4; 52/76.2, 52/726.4; 174/148, 149 R, 150
See application file for complete search history.

(56) References Cited

U.S. PATENT DOCUMENTS

| | | | | |
|---|---|---|---|---|
| 600,397 A | * | 3/1898 | Anderson | 174/45 R |
| 903,875 A | * | 11/1908 | Locke | 174/150 |
| 978,339 A | * | 12/1910 | Locke | 62/419 |
| 1,167,042 A | * | 1/1916 | Boozer | 174/149 R |
| 1,760,895 A | * | 6/1930 | Boll et al. | 337/4 |
| 1,912,456 A | * | 6/1933 | Klein | 174/33 |
| 3,260,795 A | * | 7/1966 | Bethea, Jr. | 174/144 |
| 3,467,205 A | * | 9/1969 | Wargo | 174/144 |
| 3,603,717 A | * | 9/1971 | Scott | 174/45 R |
| 3,653,622 A | * | 4/1972 | Farmer | 211/107 |
| 3,803,345 A | * | 4/1974 | Spaeth, Jr. | 174/149 R |
| 5,788,201 A | * | 8/1998 | Hardison | 248/302 |

* cited by examiner

*Primary Examiner*—Kimberly T. Wood
(74) *Attorney, Agent, or Firm*—Levine & Mandelbaum

(57) ABSTRACT

Top pole support for aerial electric power lines, in particular with suspended wires in which the aerial electric power lines have at least three wires and the top pole support has corresponding insulators, in particular suspended insulators, to hold the wires. According to the invention, the top pole support traces a continuous curve substantially passing by the points in which the insulating means are.

6 Claims, 3 Drawing Sheets

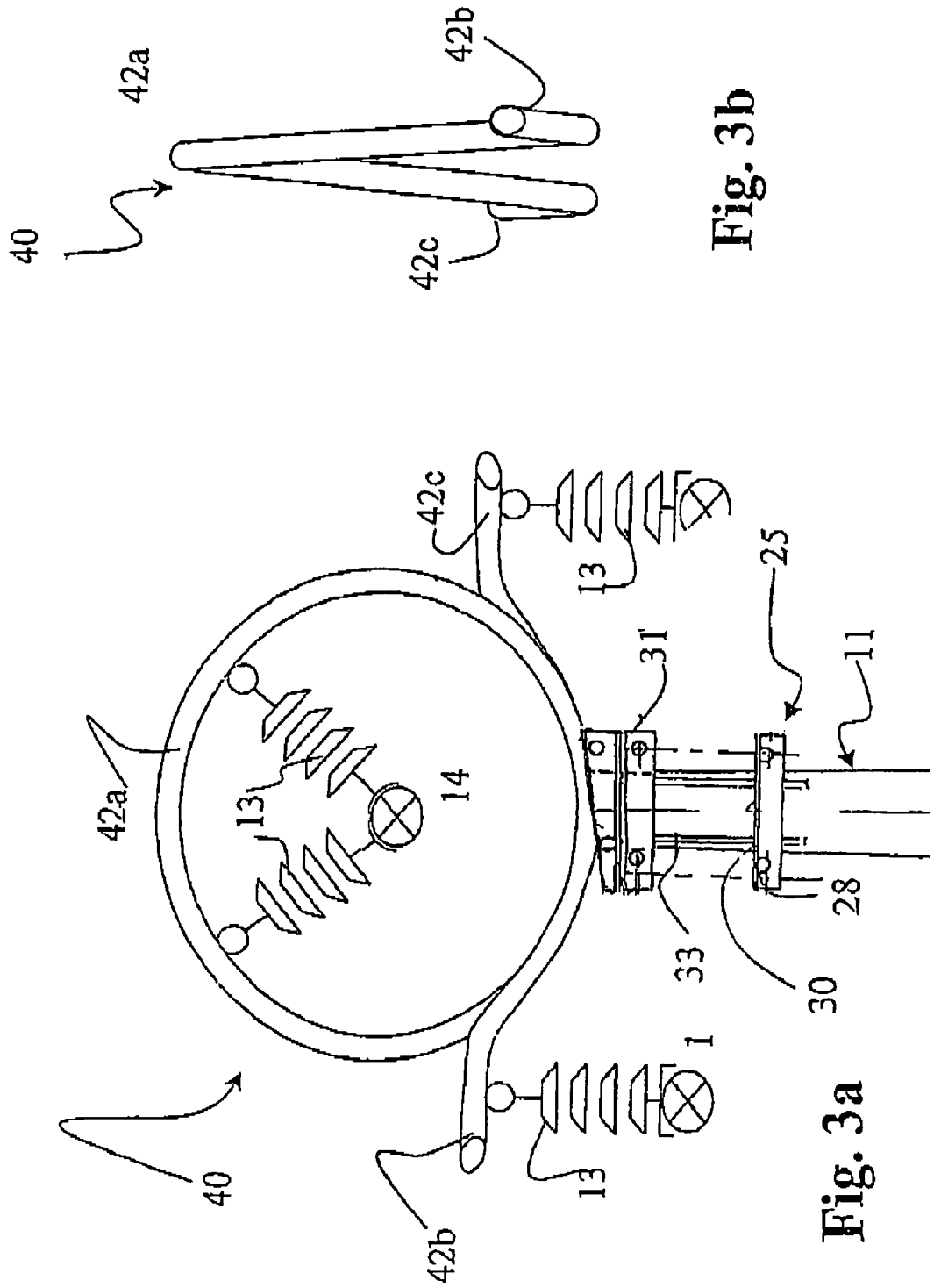

POLE TOP SUPPORT FOR AERIAL ELECTRIC POWER LINES

BACKGROUND OF THE INVENTION

The present invention relates to a top pole support for aerial electric power lines, in particular with suspended wires, in which the aerial electric power lines include at least three wires and the top pole support has insulating means, in particular suspended insulating means, to support the wires.

Aerial electric power lines for medium and high voltage, as known, are supported by suitable poles that have variety of top pole supports, i.e., supports to hold the wires of the aerial electric power lines.

The top pole supports are usually formed by a structure of straight bars, like cantilevers or a trellis, i.e., to which insulators or chains of insulators are connected to support the wires.

Medium voltage lines, in the past, used to be mounted on the top pole support via stiff insulators that were less resistant to mechanical and electrical stress than suspended insulators, i.e., hanging from the top pole support.

In order to convert lines with stiff insulators into lines with suspended insulators, it is necessary to substitute for the top pole support, one that should have the following features:

It has to support the wires at a height such that the wires are not very low along the span;

It must have an open structure in order to nest the central wire without having to cut and then splice that wire;

In FIG. 1, a top pole support 10 according to the prior art is shown mounted on the top of a pole 11, and has four arms 12a, 12b, 12c, 12d, i.e., the above mentioned straight bars. The two arms 12a and 12b perpendicularly protrude from the pole 11, in opposite directions, while arms 12c and 12d protrude in oblique directions above the pole 11, symmetrically with respect to the axis of the pole 11. Each of the four arms 12 has on its distal extremity with respect to pole 11, a chain of suspended insulators 13, to which corresponding wires 14 of the electrical aerial lines are hooked. Each of arms 12a and 12b has a chain of insulators 13 that extends downward vertically and carries a wire 14. Arms 12c and 12d have small beams 15 to which corresponding chains of insulators 13, that together support the third wire 14, are connected.

Supports known in the prior art, like the one shown in FIG. 1, have several drawbacks attributable to substantial weight and cost of the structure, that is further disadvantageously constituted by several pieces which must be assembled on the pole.

Moreover the "V" shaped chains associated to the arms 12c and 12d are too heavy and they do not stretch completely when used with the lighter wires.

Another drawback of the known supports resides in the necessity to distance insulator chains at the same height with respect to each other sufficiently to comply with specifications regarding distance between wires in the span in the presence of wind.

Also, vertical alignment of the insulator chains has to be avoided, since the formation of icicles on the wires during wintertime and their subsequent detachment provokes whip lash reactions that could short circuit two wires disposed one above the other.

The operation of changing the top pole support can be performed with the line power turned off. However, it is often more convenient to operate with voltage applied in order not to interrupt service to users. The operation of changing the top pole support requires a top pole support with a structure that allows replacement by simple and safe operations that can be performed by workers at predetermined safe distances from the wires.

SUMMARY OF THE INVENTION

The present invention has as an object to overcome the abovementioned drawbacks and to provide a top pole support for aerial electric power lines, in particular with suspended wires, having an improved construction and being more efficient than the known solutions.

Within this framework, the main object of the present invention is to provide a top pole support for aerial electrical power lines, in particular with suspended wires, suitable for simplified installation and substitution.

Another object of the present invention is to provide a top pole support for aerial electric power lines, in particular with suspended wires, that does not require peculiar assembly operations to be performed directly on the top pole.

Still another object of the present invention is to provide a top pole support for aerial electric power lines, in particular with suspended wires, that allows for an optimal spacing of the wires.

A further object of the present invention is to provide a top pole support for aerial electric power lines, in particular with suspended wires, that supports the wires at a sufficient height along the span.

Still a further object of the present invention is to provide a top pole support for aerial electric power lines, in particular with suspended wires, that has an open structure in order to receive the central wire without need for cutting and splicing the wire.

DESCRIPTION OF THE DRAWINGS

Further objects, features and advantages of the present invention will become apparent from the following detailed description and annexed drawings, which are supplied by way of non limiting example, wherein:

FIGS. 3a and 3b are two views of a variant to the top pole support shown in FIG. 2.

The inventive idea consists basically in providing a top pole support formed by a sole element that is curvilinear in order to substantially pass by the points where it is desired that the insulators supporting the wires be hooked, i.e., usually lie on the vertexes of a triangle that is placed in a way that avoids horizontal or vertical alignment of the wires.

A further feature of the invention is that the curvilinear element can have a curve that does not lie in a single plane.

DESCRIPTION OF THE PREFERRED EMBODIMENT

Figure 2:
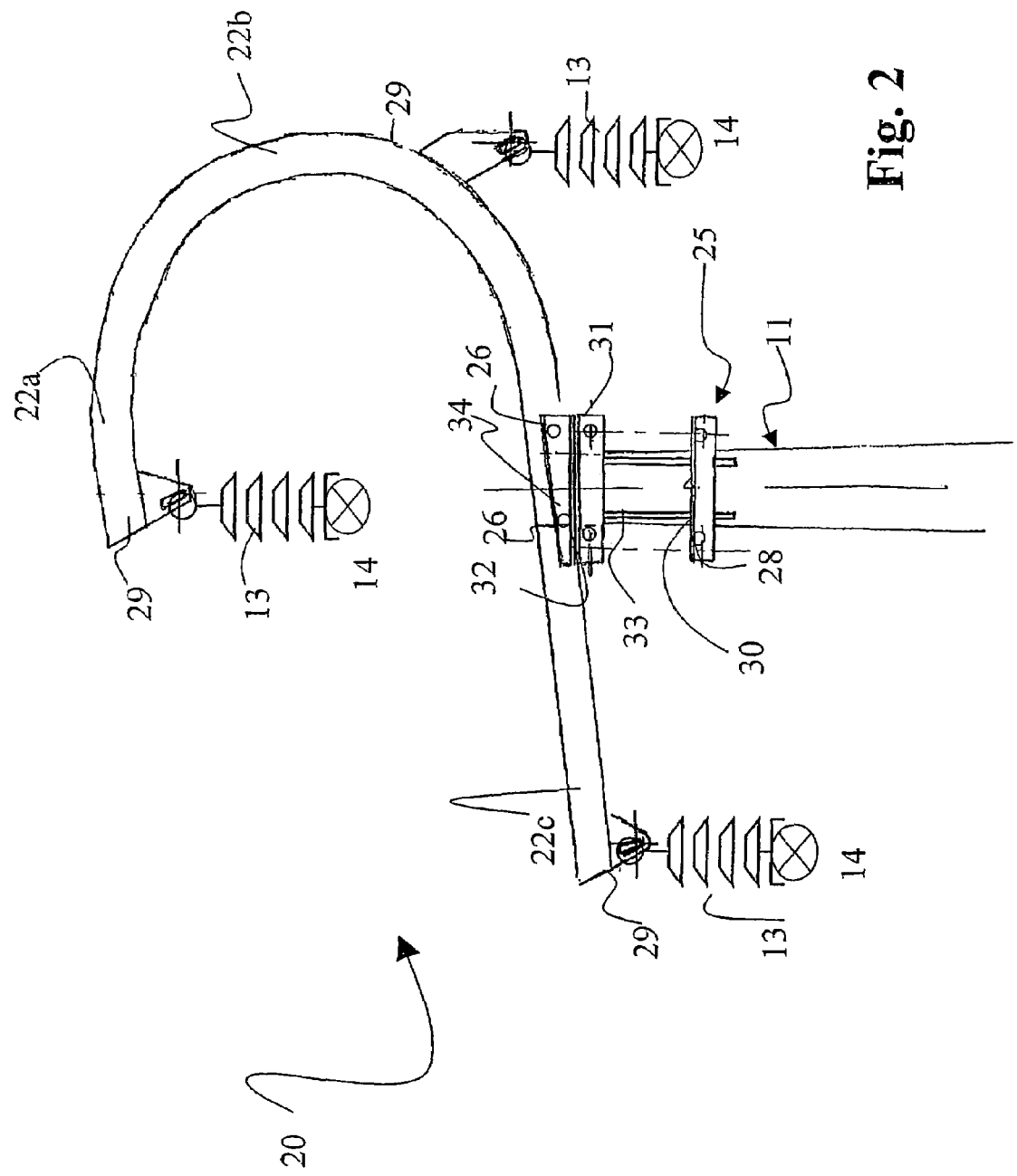
FIG. 2 is a basic diagram of a top pole support for aerial electric power lines, in particular with suspended wires, according to the invention.

In FIG. 2, a top pole support 20 for aerial electric power lines according to the invention is shown. The support 20 is shaped in a single piece, for example, a high resistance Mannesmann tube that makes a continuous curve, substantially in a shape of a reverse "C", with an upper arm 22a, a bend 22b and a lower arm 22c.

The lower arm 22c is longer than the upper arm 22a, and also slightly downwardly curved. To connections 2 on the extremities of the upper arm 22a and the lower arm 22c there are secured respective chains of suspended insulators 13 that on their distal ends support the wires 14. On an external point of the bend 22b there is similarly fixed a connection 29 for a chain of insulators 13 and a corresponding third wire 14.

Bend 22b is designed to have a shape such as to allow the chain of insulators 13 of the upper arm 22a to swing in the presence of wind, as prescribed by safety rules, without reaching the insulators swinging from the bend 22b, i.e., maintaining the correct distances among parts under voltage and grounded parts.

The top pole support 20, according to the invention, is fastened to a metallic bracket 25 through screw and bolt couplings disposed in four suitable bores 27 on the middle part of the lower arm 22c. The bracket 25 has substantially two lower clamps 30, only one of which is visible in FIG. 2, coupled together through horizontal screws 28, and two upper clamps 31, coupled together through horizontal screws 32. The upper clamps 31 and the lower clamps 30 are then coupled together through four welded vertical tubes 33. The upper clamps 31 carry on their upper part, wings 34 that are fastened to the top pole support 20 by the screw and bolt couplings 26.

When it is necessary to install the support 20 according to the invention it is possible to use a small derrick that can also be fastened to the horizontal screws 28 and 32 of the bracket 25, to lift the whole support 20, already fastened to the bracket 25, and have it reach the pole top 11, where it is leaned, fitted and fastened with a minimal effort by an operator by tightening the screws 28 and 32 through suitable bolts.

The operator, during the execution of the operation, works substantially at the height of the bracket 25, remaining conveniently far from the wires 14, that, as mentioned, can be under voltage and, during the substitution operation, moved away to a safe distance from the top of the pole 11 via insulated spikes.

Since the operator has to work only at the height of the bracket 25, without the need of climbing higher for fastening further elements, it is a lot easier for the operator to maintain control at a safe distance from the parts under voltage, both with respect to his body and with respect to the tools that he uses.

In FIGS. 3a and 3b there are shown a frontal view (FIG. 3a) and a side view (FIG. 3b) of a pole top support 40 for aerial electrical lines, which is a variation of the pole top support 20 of FIG. 2. The pole top support 40 is spirally shaped in this case, with a bend 42a and two arms 42b and 42c that are symmetric in the plane through which the spiral is viewed in FIG. 3a, i.e., a plane, transverse to the axis of the spiral, and are raised in a suitable way with respect to the point of support of the pole top support 40 in order to raise the chains of insulators 13.

The curve described by the top pole support 40, as can be better seen in FIG. 3b, where for simplicity's sake only the spiral shaped tube without the chains of insulators 13 is shown, does not lie in a single plane, but on the contrary the curve extends in space in a way that allows for insertion of the central wire without the need of cutting and then splicing it.

Figure 1:
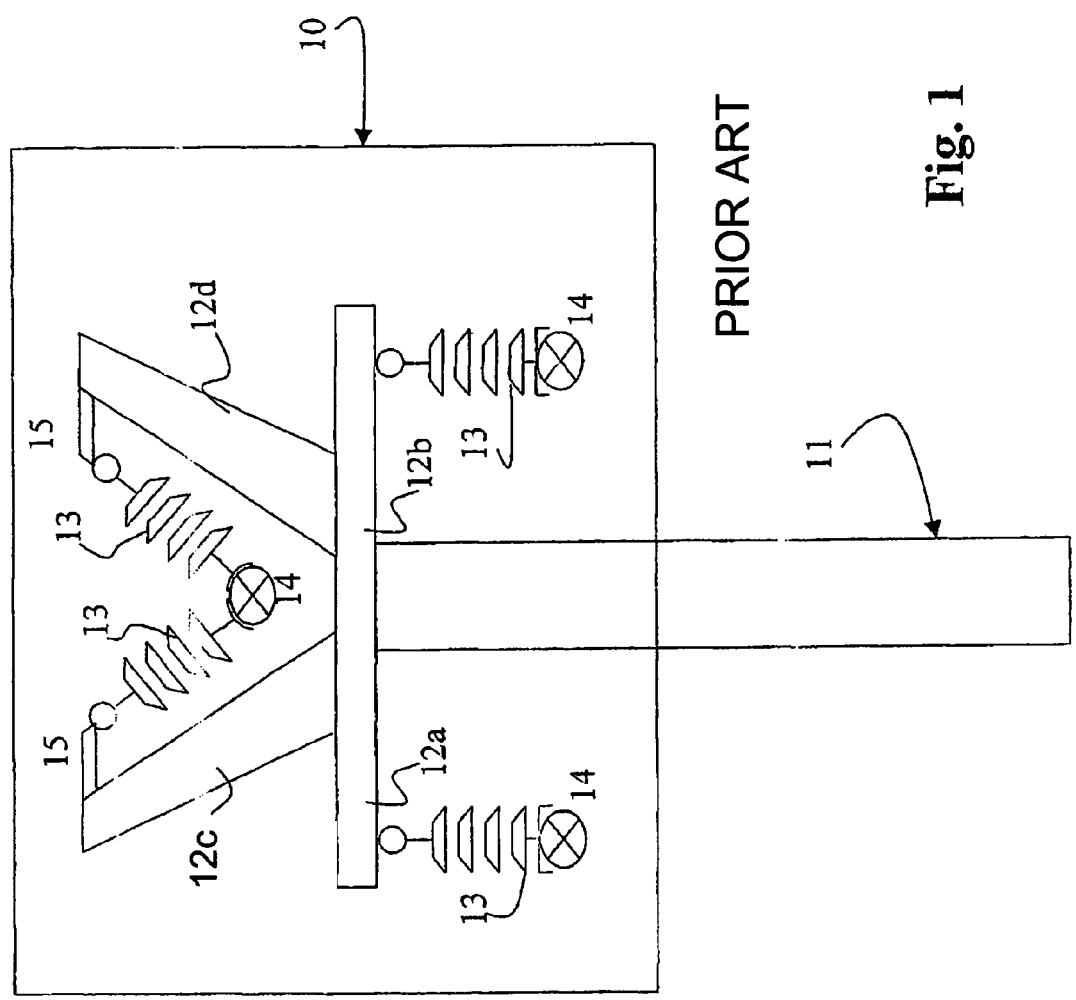
FIG. 1 is a basic diagram of a top pole support for aerial electric power lines, in particular with suspended wires, according to the prior art.

The top pole support 40, in an analogous way to the top pole support 10 shown in FIG. 1, makes use of two chains of insulators 13 on the bend 42a, that together support the third wire 14.

Of course, the top pole support 40 can also use a sole chain 13 on the bend 42a to suspend the central wire 14.

The spiral shape of the top pole support 40 gives to an intrinsically simple and light structure a remarkable mechanical resistance against stresses exerted in a direction parallel to the line direction.

From the above description the features of the present invention as well as the relevant advantages thereof are clear.

The top pole support for aerial electric power lines, in particular with suspended wires according to the invention, advantageously is obtained from a single piece that can be assembled before assembly to the pole and can be easily fastened, making installation, substitution and maintenance operations, very simple, safe and inexpensive, and possible with voltage applied.

Advantageously the "C" shape of the top pole support for aerial electric power lines, in particular with suspended wires according to the invention allows avoidance of horizontal and vertical alignments of the chains of suspended insulators, although only one element is used.

Further, advantageously, the top pole support for aerial electric power lines, in particular with suspended wires according to the invention ensures greater safety for operators during installation and substitution, since its weight can be fully supported by a lifting device such as a derrick, so that the operator need only concentrate on the fastening on the top of the pole.

Further the circular section of the tube with which the top pole support according to the invention is carried out, offers superior structural efficiency, in particular with respect to supports with cantilever straight bars, fastened through bolts.

Further, advantageously, the structure of the top pole support according to the invention is elastic, giving a higher mechanical resistance to dynamic stresses.

It is obvious that many changes will be apparent to a man skilled in the art of top pole support for aerial electric power lines, in particular with suspended wires according to the invention described above by way of example, without departing from the novelty spirit of the innovative idea, and it is also clear that in practical execution of the invention the components may often differ in form and size from the ones described, and be replaced with technically equivalent elements.

In particular, the shape of the curve described by the support can be different. In other words, it is apparent that it is possible to change the shape of the support without departing from the inventive concept of having a support obtained through a curvilinear continuous element that passes by the points where the chains of insulators that hold the wires are.

As already described, it will be possible that the curve traced by the top pole support according to the invention, by way of example, does not lie in one plane only, but it will spread in space according to the structural necessities and the placement of the chains of insulators.

The top pole support according to the invention could be carried out not only through tubes, but also through box structures or section bars.

It will be also possible, in order to match the necessities of geometry with that of safety distances, to adapt the shape of the connections and of the chains of insulators.

The top pole support can be advantageously made, all or in part, of insulating material, in order to increase insulation and, eventually, decrease the insulation of the chains that hold the wires.

The invention claimed is:

1. Top pole support for supporting three aerial electric power lines with suspended wires, on the top of a pole comprising, a bracket adapted for being mounted on the top of said pole, an elongated body with a shape that traces a continuous curve substantially passing through three mutually laterally displaced points, said curve being a continuous open curve, said body having a bend, a lower arm extending from said bend and mounted on said bracket, and an upper arm extending freely from said bend and spaced from and above said lower arm and said bracket, three insulators each connected to said body at, and suspended beneath, a respective one of said points, one of said points being on said upper arm and another of said points being on said lower arm, said upper arm and said lower arm having respective free ends separated by an open space through which a segment of one of said wires, intermediate its ends, can be passed for separating said one of said wires from said pole support without cutting said one of said wires.

2. Top pole support for aerial electric power lines according to claim 1, wherein the insulators are respectively connected adjacent to an end of the lower arm, an end of the upper arm and an external part of the bend.

3. Top pole support for aerial electric power lines according to claim 1, wherein said top pole support comprises a tubular element.

4. Top pole support for supporting three aerial electric power lines with suspended wires, on the top of a pole comprising, an elongated spiral shaped body that traces a continuous curve substantially passing through three mutually laterally displaced points, said body having a first arm at one end thereof and a second arm at an opposite end thereof, three insulators each connected to said body at, and suspended beneath, a respective one of said points, one of said points being on said first arm and another of said points being on said second arm, said first arm and said second arm having respective free ends separated by a space for enabling a segment of one of said wires intermediate its ends to separated from said pole support without cutting said one of said wires.

5. Top pole support for aerial electric power lines according to claim 4, wherein said first arm and said second arm have substantially symmetrical extremities when viewed through a plane transverse to an axis of the spiral.

6. Top pole support for at least three suspended aerial electric power lines adapted to be fastened on the top of a pole, said top pole support comprising, an elongated body shaped as a continuous open curve, having a bend and two arms with respective free ends, a bracket fastened to one of said two arms, and three horizontally laterally displaced insulating means suspended beneath corresponding points substantially belonging to said curve, said elongated body always defining a continuous open curve when fastened to the top of the pole.

\* \* \* \* \*